Figure 1:
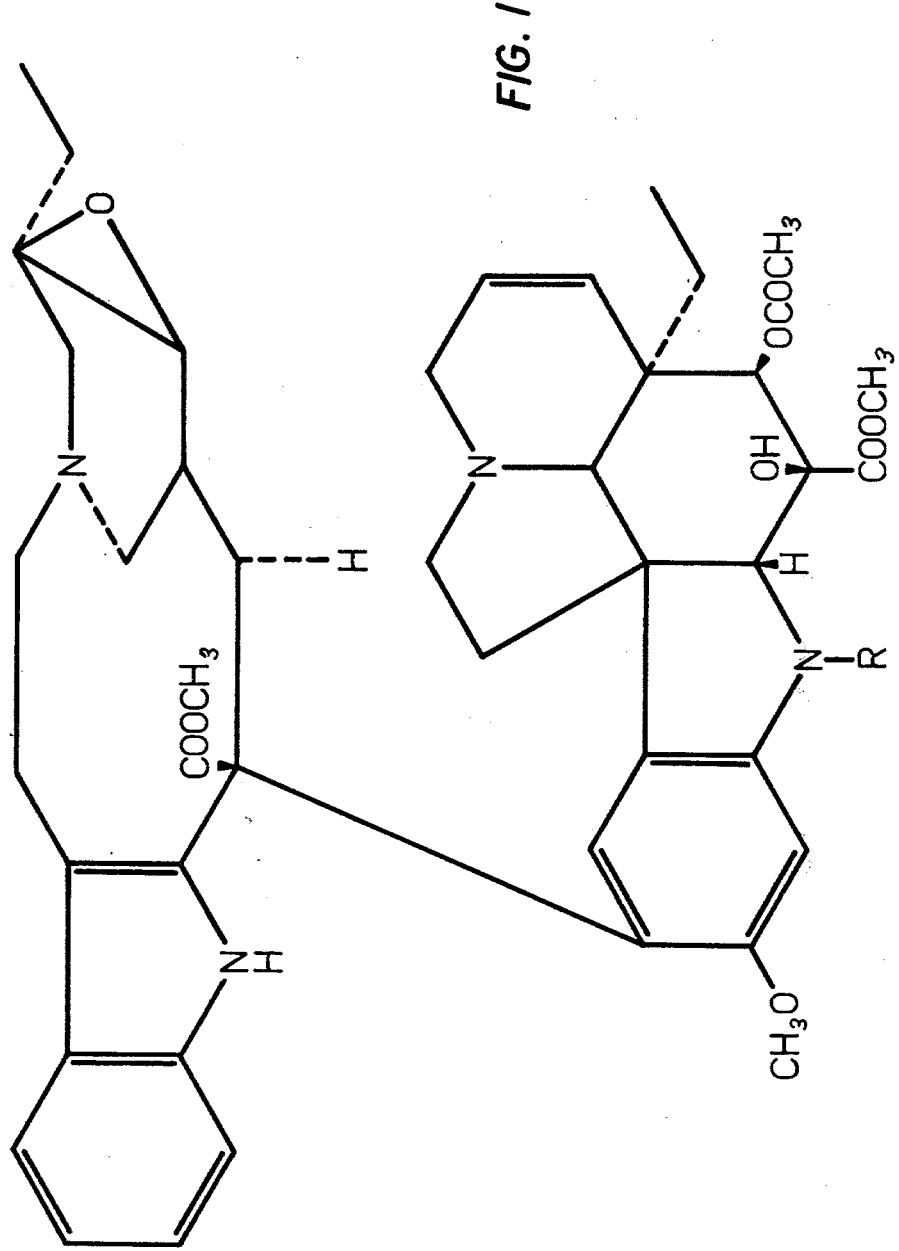

United States Patent [19]

Jovánovics et al.

[11] 4,279,915

[45] * Jul. 21, 1981

[54] METHOD OF TREATMENT USING NEW LEUROSINE DERIVATIVES

[75] Inventors: Karola Jovánovics; Kálmán Szász; Bela Kellner; Laszlo Németh; Zsuzsa Relle; Emil Bittner; Eszter Deszéri; János Éles, all of Budapest, Hungary

[73] Assignee: Richter Gedeon Vegyeszeti Gyar Rt., Budapest, Hungary

[*] Notice: The portion of the term of this patent subsequent to Jun. 2, 1998, has been disclaimed.

[21] Appl. No.: 742,463

[22] Filed: Nov. 17, 1976

Related U.S. Application Data

[63] Continuation-in-part of Ser. No. 422,100, Dec. 5, 1973, Pat. No. 4,189,432.

[30] Foreign Application Priority Data

Feb. 16, 1973 [HU] Hungary .................. RI 502

[51] Int. Cl.$^3$ .......................................... A61K 31/475
[52] U.S. Cl. .................................................. 424/262
[58] Field of Search ......................................... 424/262

[56] References Cited

PUBLICATIONS

Chemical Abstracts 81: 169686m, (1974).

Primary Examiner—Jerome D. Goldberg
Attorney, Agent, or Firm—Karl F. Ross

[57] ABSTRACT

N-formylleurosine or a pharmaceutically effective salt is used in human therapy for treatment of lymphoma, leukemia or Hodgkins Disease.

3 Claims, 3 Drawing Figures

METHOD OF TREATMENT USING NEW LEUROSINE DERIVATIVES

This application is a continuation-in-part of Ser. No. 422,100 filed Dec. 5, 1973, now U.S. Pat. No. 4,189,432 filed Feb. 19, 1980.

This invention relates to a method of treatment with pharmaceutically active leurosine derivatives of the formula (I):

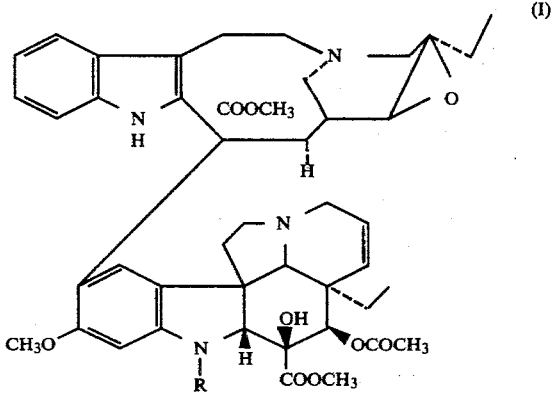

wherein R is a formyl.

In the last decades intensive research work has been carried out on the production of medicaments usable for the treatment of cancer. During this far-reaching research work substances with most diverse chemical structures have been subjected to biological and clinical investigations, but only a very limited number of these substances have proved to be curative in human therapy. Of the few pharmaceutical products which show positive results in the clinical practice, the diindole alkaloids (dimeric indole alkaloids) have proved to be important. Such diindole alkaloids are, for instance, vincaleucoblastine (vinblastine), leurocristine (vincristine), vinleurosidine (leurosidine), vinleurosine (leurosine), etc. All of these compounds were prepared, as a result of extensive research work, from the plant *Cathareanthus roseus* G. Don (or *Vinca rosea*.), of the family of Apocynaceae. These diindole alkaloids amount to about 1 to 3% of the total alkaloid content of the plant, which contains more than seventy individual alkaloids. It has been found by structural analysis that the diindole alkaloids have closely related structures. Thus, for example, vinblastine and vinchristine molecules each contain one part of velbanamine structure and another part containing a vindoline skeleton; the only difference being that the vindoline moiety of the molecule contains an N-methyl group in vinblastine, and an N-formyl group in vincristine. This minor structural difference causes, however, a significant difference in the biological activities of these compounds; namely, vincristine has proved to be more active both in animal tests, and, primarily, in human therapy.

Leurosine is different in structure from the abovementioned vinblastine or vincristine in so far as it contains an epoxy-velbanamine moiety in place of velbanamine.

The diindole alkaloids mentioned above and their acid addition salts, as well as the preparation of these compounds have been described in many publications, of which U.S. Pat. Nos. 3,097,137; 3,205,220 and 3,225,030, and Hungarian Pat. Nos. 153,200; 154,715 and 160,967 are mentioned.

In our experiments on the oxidation of leurosine we have found, unexpectedly, that leurosine can be oxidized in a fast reaction and with good yields into two compounds, namely, into N-formyl-leurosine and N-demethyl-leurosine. If desired, N-demethyl-leurosine can be converted into N-formyl-leurosine by known formylation methods.

Accordingly, this invention relates to a method using a novel and pharmaceutically active compound of the formula (I), or acid addition salts thereof—wherein R is formyl.

N-formyl-leurosine is a compound with favorable antitumor activity against lymphoma, leukemia and Hodgkins disease. Its $LD_{50}$ value is 28.8 mg./kg. (i.p., on mice), accordingly this compound is about five times less toxic than vinblastine, and about ten times less toxic than vincristine.

This compound provides complete recovery or a 300 percent extension of life span in 50 to 70 percent of the cases, in tests on mice inoculated with Ehrlich ascites carcinoma or NK/Ly lymphoma.

The treatment extends the life span of animals suffering from L-1210 lymphoid leukemia, s37 ascites sarcoma or Yoshida ascites sarcoma by about 150 to 250 percent. This compound inhibits by 70 to 80 percent the growth of solid tumors (Guerin carcinoma, S-180 sarcoma) transplanted subcutaneously. The compound of the invention causes a remarkable growth inhibition with several tumors (e.g. with Harding Passey melanoma, VX-2 rabbit epitheloma, induced and transplanted rhabdomyo-sarcoma) which could hardly be treated, if at all, with the hitherto known cytostatics, also including vinblastine and vincristine.

In animal tests this compound can be administered in a dosage of 0.3 to 5.0 mg./kg. for prolonged periods without causing side-effects characteristic of and unavoidable with the known vinca-alkaloids. The therapeutical range of this alkaloid, is, accordingly, somewhat similar to that of vincristine, and about four times broader than that of vinleurosine. A dose of 0.3 to 5.0 mg./kg. of body weight can also be used in human therapy, although the dosage can be as low as 0.01 mg./kg. daily.

The process of making the compounds consists in the following steps: leurosine, obtained by the chromatographical separation of the diindole alkaloids of the plant *Catharanthus roseus* G. Don, or a salt thereof, preferably the sulfate, is dissolved in an organic solvent or solvent mixture, preferably in a mixture of acetone and glacial acetic acid, the solution is cooled to a temperature below 0° C., preferably to −30° to −90° C., chromic acid or a chromate salt, dissolved in an organic solvent of the same temperature, preferably in acetic anhydride, is added to the above solution under intensive stirring and cooling, and the reaction mixture is allowed to stand for 5 to 15 minutes, preferably for 8 minutes. Then the reaction mixture is treated carefully with cold (−40° to −50° C.) aqueous ammonia to adjust the pH to 8 to 9, the mixture is diluted with water, and extracted with several portions of an organic solvent, preferably methylene chloride, until no alkaloid is present. The extracts are combined, washed with water, dried and evaporated to dryness under reduced pressure. A white, foam-like, amorphous dry residue is obtained, which consists mainly of N-formyl-leurosine and N-demethyl-leurosine. These compounds are separated from each other by chromatography, using a column filled with aluminum oxide (IV–V activity grade). The filling is prepared from a benzene suspension of alumina. The first eluent is benzene, and the subsequent eluents are the mixtures of benzene with different amounts of a chlorinated hydrocarbon, preferably chloroform. The substances present in the various effluent fractions are identified by thin layer chromatography. First the accompanying substances leave the column, then N-demethyl-leurosine, and finally N-formyl-leurosine is eluted. The fractions containing identical substances are combined, evaporated to dryness under reduced pressure, and, if desired, the obtained bases are converted into their acid addition salts, preferably into the corresponding monosulfates. The compounds can be purified by recrystallization, if desired. This purification method is applied primarily to the salts. N-demethyl-leurosine can be formylated by known methods (see C. W. Huffman: J. Org. Chem. 23, 727; 1958) to yield N-formyl-leurosine.

According to a preferred method of the invention one proceeds as follows: the dry residue, obtained in the processing of the reaction mixture of oxidation, is formylated with a mixture of formic acid and acetic anhydride. In this reaction N-demethyl-leurosine is converted into N-formyl-leurosine. The reaction mixture is neutralized, extracted with methylene chloride, the extract is washed with water, and evaporated to dryness under reduced pressure. The obtained dry residue is purified by chromatography. The obtained N-formyl-leurosine is converted optionally into its salt, preferably into the sulfate, and the salt is recrystallized, if desired.

The invention is elucidated in detail by the following Examples.

EXAMPLE 1

12 g. (0.0132 moles) of leurosine sulfate are dissolved in 2640 ml. of acetone, thereafter 0.1 l. of glacial acetic acid, freshly distilled from a mixture containing chromic acid, are added. The solution is cooled to $-55°$ C., and cold acetic anhydride, containing 5.94 g. (0.135 moles) of chromic acid, are added to the stirred mixture within 3 minutes. The mixture is left to stand for further five minutes, then the pH of the solution is adjusted to 6 using cold concentrated aqous ammonia. This operation is carried out within 7 minutes, and requires about 6 l. of ammonia solution. During this neutralization the mixture is cooled in order to prevent the temperature from rising above $+50°$ C. The obtained mixture is filled into a glass vessel equipped with a glass stirrer and an outlet tap, which already contains 9 l. of distilled water. The diluted solution is rendered alkaline with further amounts of aqueous ammonia, to set pH=8.5.

Thereafter the reaction mixture is extracted with 4×1.5 l. of methylene chloride. The alkaloid bases are transferred into the methylene chloride phase. The phases are separated, the organic solutions are combined, and washed with 3×1 l. of distilled water for removing ammonium acetate formed in the neutralization step. Thereafter the organic phase is dried over sodium sulfate, and evaporated to dryness under reduced pressure.

10 g. of a beige-white dry residue are obtained; the product is a crude mixture of N-formyl-leurosine and N-demethyl-leurosine.

The dry residue is dissolved in 60 ml. of benzene, and the solution is poured onto a chromatographic column with a diameter of 35 mm., filled with 500 g. of aluminum oxide (IV–V activity grade). The filling is prepared from a benzene suspension of aluminum oxide.

The column is eluted with the solvents or solvent mixtures listed in Table 1.

TABLE 1

| Composition of eluting agent | Amount of eluting agent ml. |
| --- | --- |
| Benzene | 900 |
| 9:1 mixture of benzene and chloroform | 1800 |
| 8.5:1.5 mixture of benzene and chloroform | 1000 |
| 8:2 mixture of benzene and chloroform | 2800 |
| 1:1 mixture of benzene and chloroform | 2800 |
| Chloroform | 800 |

The effluent is collected into fractions each of 400 ml. volume. The various fractions are examined by thin layer chromatography (Fransworth, M. R. et al.: Lloydia, 27, 302 (1964)).

Fractions 1 to 5 do not contain alkaloids. The first traces of alkaloid appear generally in fraction 6, which contains mainly unreacted leurosine. N-demethyl-leurosine generally appears first around fraction 7, and is eluted completely until about fraction 15. The elution of N-formyl-leurosine starts at about fraction 13, and terminates generally around fractions 19-21.

The fractions which, on the basis of thin layer chromatographical analysis, contain the same alkaloids are combined, and evaporated to dryness under reduced pressure.

5.6 g. of crude, amorphous N-formyl-leurosine and 1.5 g. of crude, amorphous N-demethyl-leurosine are obtained.

In the next step these crude, amorphous bases are converted separately into their monosulfates. One part by weight of the crude product is dissolved in 5 part by volume of dry ethanol, thereafter the solution is acidified to pH 4 by adding a one percent sulfuric acid solution in dry ethanol. The separation of the crystalline sulfate starts immediately. The mixture is allowed to stand at room temperature for several hours, and then the separated crystals are filtered off. The salts are then recrystallized as follows: one part by weight of the crystalline sulfate is dissolved in 5 parts by volume of methanol, and the volume of the solution is increased to fivefold with dry ethanol. The solution is allowed to stand at room temperature, then the separated product is filtered off, washed with dry ethanol, and dried.

In this process the following substances are obtained: 4.8 g. (40.1%) of N-formyl-leurosine monosulfate, m.p.: 248°-252° C. (Boetius), $(\alpha)_{20}^D = +37°$ (c=1, in water); and 1.1 g. (9.3%) of N-demethyl-leurosine monosulfate; decomposes without melting; $(\alpha)_{20}^D -3.2°$ (c=1, in water).

In order to determine the physical constants of the N-formyl-leurosine base, a part of the thus obtained N-formyl-leurosine monosulfate is dissolved in water, the pH of the solution is adjusted to 8 to 9 with concentrated aqueous ammonia, and the mixture is extracted three times with methylene chloride. The organic phases are combined, dried and evaporated to dryness under reduced pressure. The obtained amorphous N-formyl-leurosine is recrystallized from methanol. The crystalline N-formyl-leurosine melts at 209°-211° C. (Boetius); $\alpha_{20}^D = 80.3°$ (c=1, in chloroform).

Figure 2:
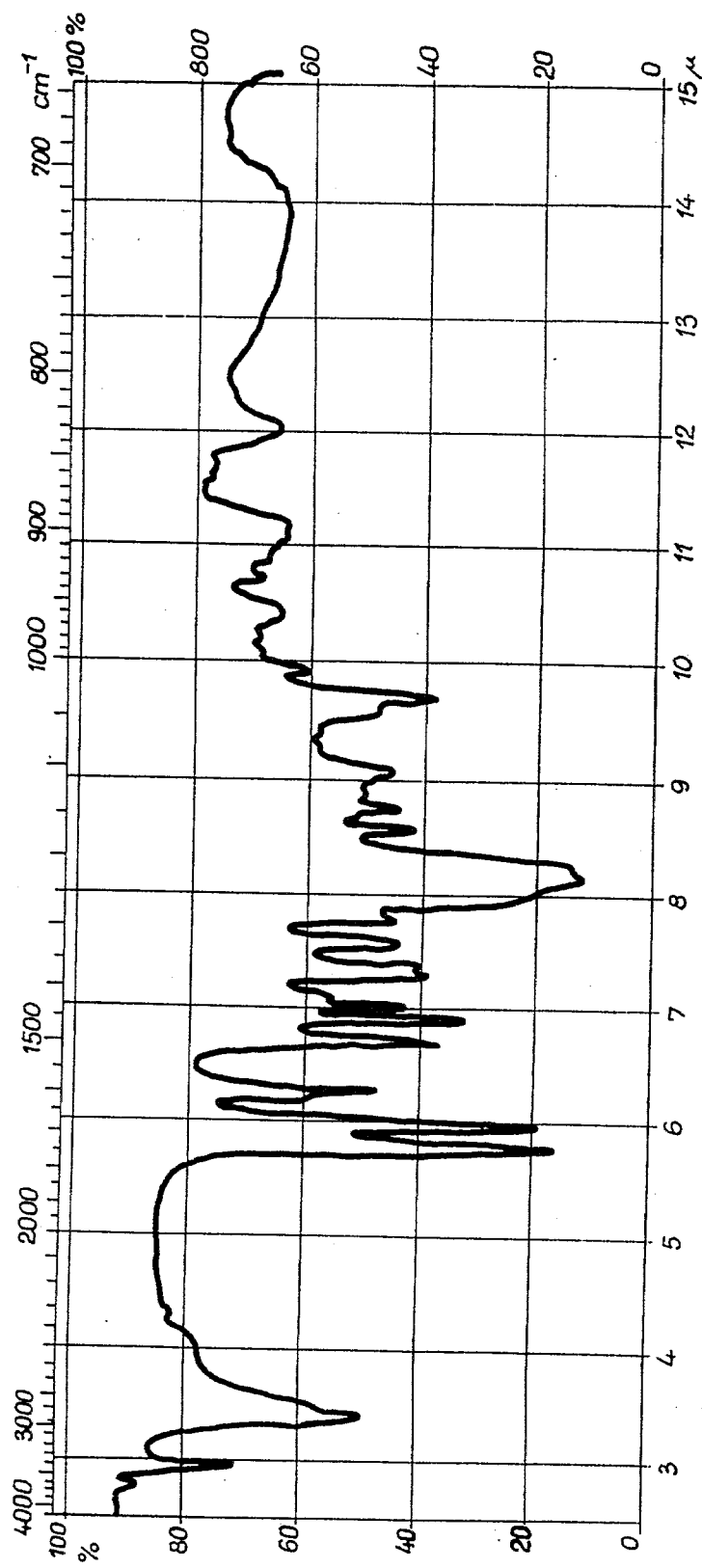

The IR spectrum of N-formyl-leurosine is shown in FIG. 2. This spectrum is different from that of leurosine in the strong absorption band of the formyl group, which appears at 1672 cm$^{-1}$.

On the basis of the mass spectrum, the mass number of the N-formyl-leurosine molecule ion is 822. The measured exact mass is M=822.3977, from which the empirical formula $C_{46}H_{54}N_4O_{10}$, with the theoretical mass of 822.3909, can be calculated.

Analysis: Calculated for $C_{46}H_{54}N_4O_{10}$: C: 67.15%, H: 6.61%, N: 6.81%, O: 19.43% Found 66.95%, H: 6.58%, N: 6.75%, O: 19.27%.

This molecule ion gives rise to an ion peak with mass number 793, corresponding to the removal of the formyl group, as is proved by the exact mass $$m/e_{measured} = 793.3866.$$

The empirical formula corresponding to this mass number is $C_{45}H_{53}N_4O_8$, with a calculated mass of $$m/e_{calculated} = 793.3882.$$

Similarly to the mass spectrum of the leurosine base, the ion peak corresponding to mass number 353 also appears in the mass spectrum of the N-formyl-leurosine base, which corresponds to the epoxyvelbanamine moiety. This fact has also been proved by the measurement of the exact mass:

$$m/e_{measured} = 353.1874,$$

which corresponds to the empirical formula of $C_{21}H_{25}N_2O_3$, with a calculated mass of $$m/e_{calculated} = 353.1858.$$

In order to determine the physical constants of the N-demethyl-leurosine base, N-demethyl-leurosine monosulfate is dissolved in water, the pH of the solution is adjusted to 8 to 9 with aqueous ammonia, and the liberated base is extracted with methylene chloride. The organic phases are combined, dried and evaporated to dryness. The amorphous, dry residue is recrystallized from methanol.

Crystalline N-demethyl-leurosine has the following physical constants: m.p.: 208°–210° C. (Boetius); $\alpha_{20}{}^D = +50.1°$ (c=1, in chloroform).

Figure 3:
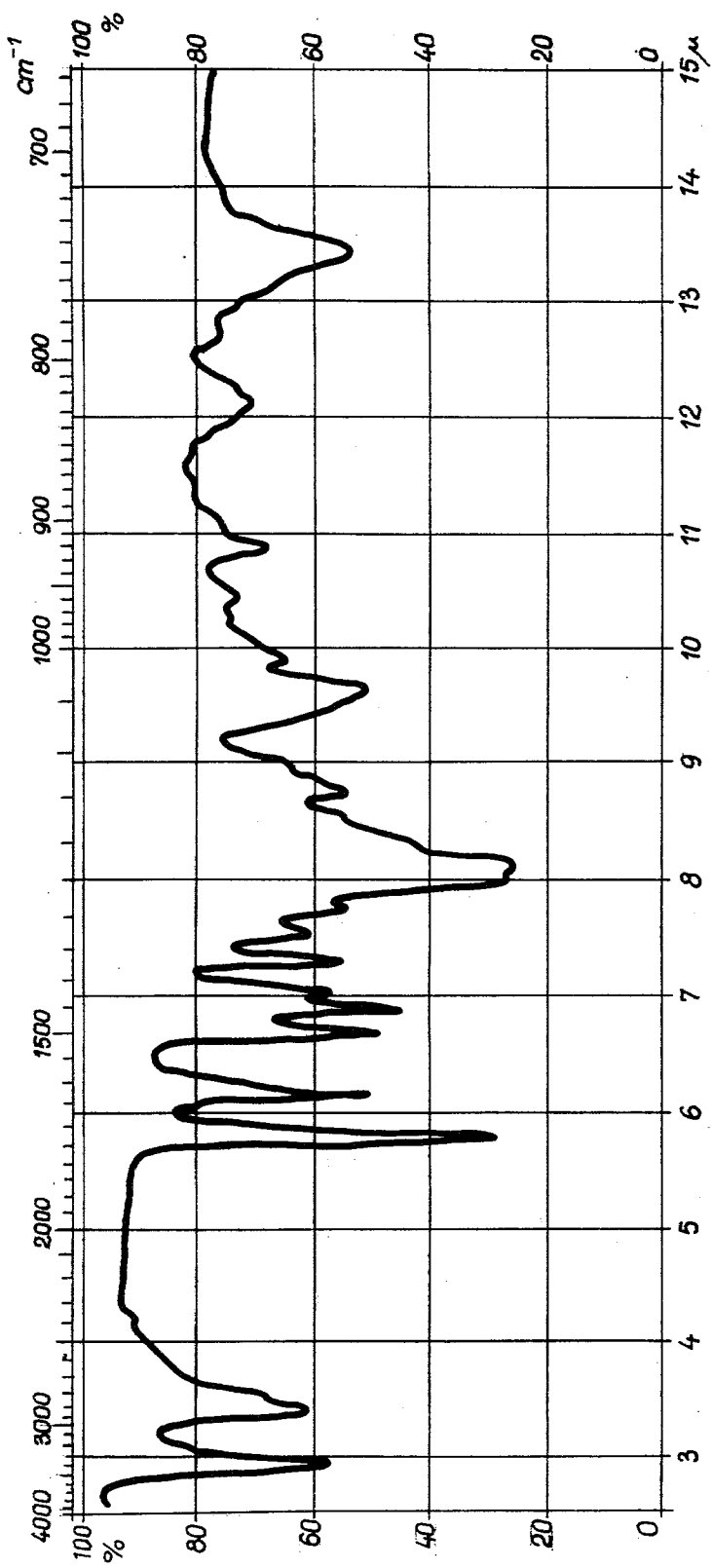

The IR spectrum of N-demethyl-leurosine is given in FIG. 3. This spectrum is different from that of leurosine in the strong absorption band of the secondary amine group, formed upon demethylation, appearing at 3350 cm$^{-1}$.

On the basis of the mass spectrum, the mass number of the N-demethyl-leurosine molecule ion is 794. From the exact mass number given below, the empirical formula $C_{45}H_{54}N_4O_9$ can be calculated.

Analysis: Calculated for $C_{45}H_{54}N_4O_9$: C: 68.00%, H: 6.85%, N: 7.05%, O: 18.10% Found: C: 67.85%, H: 6.79%, N: 6.90%, O: 17.95%.

Measured mass $$m/e_{measured} = 794.3895.$$

On the basis of the above formula $$m/e_{calculated} = 794.3882.$$

EXAMPLE 2

1 g. of N-demethyl-leurosine is dissolved in the mixture of 6 ml. of concentrated formic acid and 1 ml. of acetic anhydride, and the mixture is left to stand at room temperature for 10 minutes. Thereafter the mixture is poured into 30 ml. of cold (0° to 5° C.) water, and the pH of the mixture is adjusted to 9.0 with cold, concentrated aqueous ammonia. The ammonia solution is added under stirring. The alkaloid is extracted from the aqueous solution with 3×30 ml. of methylene chloride. The methylene chloride solutions are combined, dried and evaporated to dryness under reduced pressure.

0.95 g. of amorphous, white N-formyl-leurosine are obtained, which is converted into its monosulfate as described in Example 1. In this reaction 1.01 g. of N-formyl-leurosine monosulfate are obtained.

EXAMPLE 3

10 g. of a beige-white, foam-like crude residue consisting of N-formyl-leurosine and N-demethyl-leurosine obtained by oxidizing 12 g. (0.0132 moles) of leurosine sulfate as described in Example 1 are dissolved in a mixture of 60 ml. of concentrated formic acid and 10 ml. of acetic anhydride, and the mixture is poured, under stirring into 300 ml. of cold (0° to 5° C.) water. The pH of the mixture is adjusted to 9.0 with cold, concentrated aqueous ammonia, under stirring. The solution is extracted with 3×100 ml. of methylene chloride. The methylene chloride phases are combined, dried, and evaporated to dryness under reduced pressure. 9.8 g. of amorphous, white, crude N-formyl-leurosine are obtained.

The obtained crude N-formyl-leurosine is purified by column chromatography. The crude product is dissolved in 60 ml. of benzene, and this solution is charged onto a column of 45 mm. diameter, filled with 500 g. of aluminum oxide (III activity grade) in benzene. The column is eluted with the solvents listed in Table 2.

TABLE 2

| Composition of the eluting agent | Amount of the eluting agent, ml. |
|---|---|
| Benzene | 1200 |
| 2:1 mixture of benzene and chloroform | 5000 |
| 1:1 mixture of benzene and chloroform | 3000 |
| Chloroform | 800 |

The effluent is collected into fractions each of 400 ml. volume.

Fractions 1 to 3 do not contain alkaloids. Fractions 4 to 10 contain the accompanying materials. Starting at about fraction 11, N-formyl-leurosine also appears in addition to the accompanying substances. Approximately fractions 15 to 20 contain N-formyl-leurosine alone. In the subsequent fractions the amount of eluted N-formyl-leurosine gradually decreases. The fractions which contain N-formyl-leurosine alone are combined and evaporated to dryness under reduced pressure. 6.5 g. of crude, amorphous N-formyl-leurosine are obtained.

This crude, amorphous N-formyl-leurosine base is converted into its monosulfate as follows: 6.5 g. of N-formyl-leurosine are dissolved in 32.5 ml. of dry ethanol, thereafter the solution is acidified to pH 4 by adding a 1% sulfuric acid solution in dry ethanol. The separation of the crystalline substance starts immediately. The mixture is left to stand at room temperature for several hours, thereafter the crystals are filtered off and washed with dry ethanol, 6.5 g. of crystalline N-formyl-leurosine monosulfate are obtained.

The eluates collected before and after the fractions containing pure N-formyl-leurosine contain accompanying substances and N-formyl-leurosine. These fractions are combined and evaporated to dryness. The amorphous substance (1.75 g.) obtained this way is dissolved in benzene, and purified by chromatography as described above, with the only difference that in order to ensure a better separation the column is eluted with 1200 ml. of a 2:1 mixture of benzene and chloroform. The fractions containing N-formyl-leurosine alone are processed as described above, to yield a further 1.05 g. of pure, crystalline N-formyl-leurosine monosulfate. Total yield: 7.10 g. (63.7%) of N-formyl-leurosine monosulfate. The physical constants of this compound are identical with those given in Example 1.

EXAMPLE A

Based on the experiences obtained on 17 patients during the first half-year, further 8 patients with haemoblastoses and leukemia were given treatment. The patients were given daily 0.05 mg/kg single doses. The clinical examinations during the second half-year were performed with the same daily dose, but with different total doses. The smallest total amount meant 3, the highest 12 subsequent doses. The dosage was tested both in forms of sequential and intermittent treatment.

3 patients out of 8 received the drug sequentially, which meant single doses on subsequent days, the remaining 5 patients were given intermittent treatment.

The intermittent treatment was made in two ways: 1. Single doses through 3 days, followed by 5 days interval as total up to an amount of 12 times 0.05 mg/kg. 2. Single dose on the first day, followed by 3 days interval, up to a total amount of 12 times 0.05 mg/kg.

The route of administration was always intravenous, 1 mg active substance was dissolved in 10 ml physiological saline.

| Distribution of the patients: | |
|---|---|
| Acute lymphoid leukemia | 1 patient |
| Acute myeloid leukemia | 1 patient |
| Hodgkin disease | 1 patient |
| Reticulosarcoma | 1 patient |
| Lymphosarcoma | 1 patient |
| Myeloma multiplex | 1 patient |
| Chronic lymphoid leukemia, sarcomaform | 2 patients |
| | 8 patients |

With the dose described above, all complete treatments were followed by objective improvement, and both leukemic patients had complete remission.

In summary it can be established that N-formyl-leurosine is a very effective cytostatic. In the course of the phase I examinations it is equally effective in acute leukemia (myeloblast and lymphoblast type), and in lymphomas. In 0.05 mg/kg daily dose, applied 3-12 times it does not produce any side effects. No untoward symptoms of a neurological respect appear.

EXAMPLE B

N-formyl-leurosine was administered in form of i.v. injection as single treatment or in 5 and 2×5 day long periods continually to exclusively patients with solid tumors.

Simultaneously adjuvant therapy was applied (analgesics, antibiotics, cardiac drugs, roborants) if necessary.

Following single treatments primarily the effect on blood picture, and especially on leukocyte count was observed. In case of higher total doses given continuously for 5 or 10 days, liver function, enzymes, serum creatinine, uric acid level were also determined. The neurological condition of the patients was also controlled.

Results

1. In tumor growth: first of all some effect was observed with the continuous administration of 0.018-0.035 mg/kg doses. In one case slight regression evidence by X-ray and touching (0.030 mg/kg during 2×5 days), in one case express progress during the treatment (0.018 mg/kg during 2×5 days) could be observed. No changes were found in other cases.

2. In the blood picture: in the first 48 hours the leukocyte count increased, between the 3rd and 5th days it decreased again, but remained over 3000, and between the 9th and 14th days returns to the initial value. At the dose level presently used no change was shown in the qualitative blood picture.

3. In liver function, urinalysis, serum creatinine and uric acid levels no changes or signs indicating toxicity were found.

4. The levels of various enzymes (serum alk, phosphatase, SGOT, SGPT) did not essentially change during the treatment.

5. The prothrombin-time increased in three cases out of six, at the same time the prothrombin index and activity decreased in one case by 50, in two cases by 37% by the 7th day of the treatment. In two cases the prothrombin time very slightly decreased.

6. Neurological side-effects were not observed.

Table I shows the effect of N-formyl leurosine on different types of leukaemia. In contrast to the drug's beneficial effect in acute leukaemias, in cases of chronic lymphocytic leukaemia no haematological remission could be induced but some clinical improvement was achieved in all the 3 CLL patients. In the first case (SZ. L.) splenomegaly diminished, in the second one (T. B.) enlargement of pathological lymph nodes became less pronounced, in the third case both the lymph nodes and the spleen increased in volume.

The bottom of the table gives the most important data related to the four cases of acute leukaemia of four different cell types. Complete haematological remission was achieved in two cases, one of the patients suffered from ALL, the other from AML, Clinical improvement, parallel with the haematological one, was observed only in the case of the ALL patient. The AML patient died one month after the end of the treatment.

In the case of the ALL patient complete haematological remission developed by the 10th day after the beginning of treatment, and lasted 2 months. The AML patient went into remission on the 8th day of treatment but 14 days after finishing it she fell into relapse which was untreatable because of serious thrombopenia and consequent bleeding.

Data of patients suffering from different types of lymphoma are shown in Table II. Both of Hodgkin patients belonged to the poor risk category. One of the poor risk patients (Zs. A.) proved to be sensitive to N-formyl-leurosine treatment. Comparing the X-ray picture of the chest before and after the treatment an undoubted improvement in the intensity and size of the atelectasia in the lower region of the right lung was noticeable.

4 patients of lymphosarcoma were treated, one of them, P. D. received two courses. Patient P. D. had enlarged pathological lymph nodes in all peripheral regions. After finishing the second course of treatment, all but one of the palpable lymph nodes disappeared. The Westergren value, 75 mm/hour before the treatment, fell to 12 mm/h. Patient D. N. was also successfully treated. The majority of his palpable lymph nodes disappeared. Change in mediastinal pathologic lymph nodes' size and intensity is not spectacular, but definite. A moderate remission was developed by one patient (T. I.), the only non-responding lymphosarcoma patient (C. J.) belonged to the poor risk category.

Out of two reticulosarcoma patients one showed a moderate improvement after therapy; some of her lymph nodes diminished in volume, became softer and more mobile.

TABLE I
EFFECT OF F-LEUROSINE ON LEUKAEMIAS

| PATIENT | DIAGNOSIS | SCHEDULE | EFFECT HAEMATOL. | CLINICAL |
|---|---|---|---|---|
| SZ.L. | 71 woman | CLL | A | — | + |
| T.B. | 74 man | CLL | A | — | + |
| F.I. | 46 man | CLL | A | — | + |
| F.M. | 52 woman | AML | A | CR | — |
| SZ.I. | 31 man | ALL | C | CR | + |
| SZ.A. | 67 woman | AMoL | C | IR>50% | + |
| B.I. | 57 woman | AUL | C | IR>50% | + |

TABLE II
EFFECT OF F-LEUROSINE ON LYMPHOMAS

| PATIENT | DIAGNOSIS | SCHEDULE | EFFECT |
|---|---|---|---|
| H.I. | 34 woman | Hodgkin Dis. | A | — |
| ZS.A. | 30 woman | Hodgkin SC. | C | IR<50% |
| P.D. | 42 man I | Lysc. | A | IR>50% |
| P.D. | 42 man II | Lysc. | B | IR<50% |
| T.I. | 70 man | Lysc. | A | IR<50% |
| D.N. | 78 man | Lysc. | C | IR>50% |
| G.J. | 42 man | Lysc. | A | — |
| B.B. | 72 woman | Rsc. | C | IR<50% |
| Cs.A. | 27 woman | Rsc. | A | — |

In the following F-leurosine means N-formyl-leurosine.

TABLE III
ACUTE TOXICITY IN SWISS MICE

| Agent | LD$_{50}$ mg/kg i.p. | 1 x i.v. |
|---|---|---|
| Vincristine | 4,0 | 3,0 |
| Vinblastine | 7,6 | 15,0 |
| F-Leurosine | 28,8 | 32,5 |

Table III lists the comparative toxicological data concerning Vincristine, Vinblastine and F-leurosine. The new analogue is approximately 7 times less toxic than Vincristine and 4 times less toxic than Vinblastine in acute rodent experiments. It is remarkable to note, that even subluthal doses did not show any signs of neurotoxicity on any of the experimental animals.

TABLE IV
EFFECT OF F-LEUROSINE ON ASCITIC TUMORS

| Tumor | Dosage mg/kg i.p. | Schedule | Survival | Tumor inhibition | Tumor free |
|---|---|---|---|---|---|
| NK/ly | 8 × 0.5 | daily | 250 | — | 2/10 |
| Ehrlich cc. | 24 × 0.15 | daily | 118 | — | 3/10 |
| | 4 × 0.6 | each other day | 288 | — | 7/10 |
| | 7 × 3.0 | daily | 244 | — | 3/10 |
| S 37 | 4 × 2.5 | daily | | 100 | 4/6 |
| | 8 × 1.0 | daily | 268 | | 1/6 |
| Yoshida sarc. | 9 × 0.5 | daily | 143 | | 0/6 |
| | 9 × 1.0 | daily | 173 | | 2/6 |
| | 9 × 2.0 | daily | 243 | | 4/6 |
| Novikoff | 6 × 2.0 | daily | 166 | | 0/6 |
| | 4 × 3.0 | each other day | 196 | | 1/6 |

TABLE V
EFFECT OF F-LEUROSINE ON L 1210 I.P. LEUKEMIA ON BDF$_1$ MICE

| DOSAGE mg/kg i.p. | Schedule | Mean survival in days | Survival |
|---|---|---|---|
| 8 × 1.25 | daily | 27.7 | 131 |
| 8 × 2.5 | daily | 25.0 | 127 |
| 8 × 5.0 | daily | 23.0 | 109 |
| 8 × 7.5 | daily | 19.5 | 56 tox |
| 8 × 2.5 | 48 hr interval | 22.4 | 137 |
| 8 × 5.0 | 48 hr interval | 24.0 | 126 |
| 8 × 10.0 | 48 hr interval | 21.7 | 60 tox |
| 8 × 2.5 | 72 hr interval | 12.0 | 48 |
| 8 × 5.0 | 72 hr interval | 22.1 | 123 |
| 8 × 7.5 | 72 hr interval | 20.2 | 117 |
| 8 × 10.0 | 72 hr interval | 22.3 | 145 |
| 8 × 5.0 | 96 hr interval | 10.8 | 35 |
| 8 × 7.5 | 96 hr interval | 19.2 | 95 |
| 8 × 10.0 | 96 hr interval | 23.6 | 136 |

L-1210 leukemia in BDF$_1$ mice was also sensitive to the treatment. Small doses administered daily or high doses given twice weekly are equally potent.

The haematological parameters showed an interesting pattern. The number of granulocytes was lowered by 50% if 0.6 mg/kg Formyl-Leurosine was given, while that of the lymphocytes decreased only after administration of 15 mg/kg. No significant changes were observed in the platelet count at similar dose level.

On the basis of these and several other findings a Phase I trial was initiated.

Fourteen patients were treated. The patient selection met the following criteria: (a) all types of leukemia, (b) all patients previously treated without success, (e) no X-ray or chemotherapy was administered four weeks prior to therapy, (d) at least eight weeks follow-up. In the escalation period 0.01 mg/kg/day i.v. was given five consecutive days as initial dose. This dose was gradually increased up to 0.05 mg/kg/day i.v. six consecutive days. At this level striking antitumor activity was revealed without signs of toxicity.

TABLE VI
DOSAGE OF F-LEUROSINE IN PHASE I TRIAL (EVALUATION PERIOD)

| Dose/i.v./ mg/kg | No. of patients | Antitumor effect | Side effect |
|---|---|---|---|
| 0.05 × 9–12 | 7 | + | — |
| 0.08 × 9–12 | 7 | + | — |
| ↑↑↑ | ↑↑↑ | ↑↑↑ | ↑↑↑ |
| Days 1–3 | 8–10 | 15–17 | 22–24 |

In the evaluation period patients received F-Leurosine as demonstrated above. In addition, eight patients were added to the group treated on the basis of this schedule.

Therapeutic results obtained by F-Leurosine in leukemias and haemoblastoses are listed in Table VII.

TABLE VII

Therapeutic Results Obtained by F-Leurosine Treatment

| | No. of patients | Complete remission | Partial remission | No response |
|---|---|---|---|---|
| AML | 1 | 1 | — | — |
| ALL | 1 | 1 | — | — |
| AUL | 1 | — | 1 | — |
| AMoL | 1 | — | 1 | — |
| CLL | 3 | — | 3 | — |
| Hodgkin's disease | 2 | — | — | 2 |
| LSC | 5 | — | 4 | 1 |
| RSC | 2 | — | 1 | 1 |
| Multiple myelomo | 6 | — | 4 | 2 |
| Total: | 22 | 2 | 14 | 6 |

We claim:

1. A method of treating leukemia, lymphomas or Hodgkin's disease in human patients comprising administering to a human patient a cytostatically effective amount of a compound effective amount of a compound of the formula I,

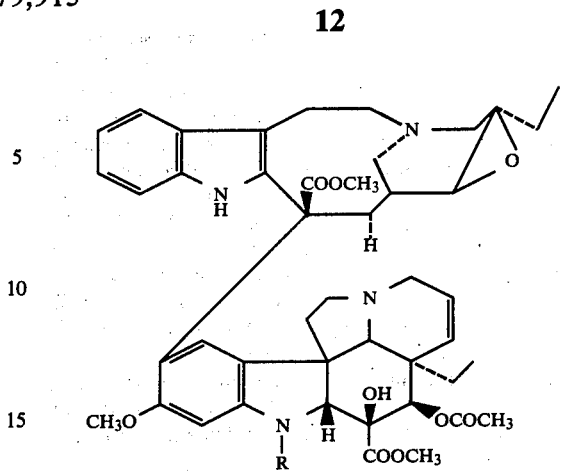

wherein R is formyl, or a pharmaceutically acceptable acid addition salt thereof.

2. The method defined in claim 1 wherein said compound is N-formyl-leurosine.

3. The method defined in claim 1 wherein said compound is N-formyl-leurosine monosulfate.

* * * * *